(12) United States Patent
Liu et al.

(10) Patent No.: US 11,523,893 B2
(45) Date of Patent: Dec. 13, 2022

(54) COVERED STENT

(71) Applicant: LIFETECH SCIENTIFIC (SHENZHEN) CO., LTD, Shenzhen (CN)

(72) Inventors: Caiping Liu, Shenzhen (CN); Zhen Li, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 59 days.

(21) Appl. No.: 16/640,868

(22) PCT Filed: Aug. 22, 2018

(86) PCT No.: PCT/CN2018/101738
§ 371 (c)(1),
(2) Date: Feb. 21, 2020

(87) PCT Pub. No.: WO2019/042201
PCT Pub. Date: Mar. 7, 2019

(65) Prior Publication Data
US 2020/0188083 A1      Jun. 18, 2020

(30) Foreign Application Priority Data
Aug. 28, 2017   (CN) .................... 201710749682.X (51) Int. Cl.
   *A61F 2/06*       (2013.01)
   *A61F 2/90*       (2013.01)
   *A61F 2/852*      (2013.01)
(52) U.S. Cl.
   CPC ............... *A61F 2/06* (2013.01); *A61F 2/852* (2013.01); *A61F 2/90* (2013.01); *A61F 2002/065* (2013.01); *A61F 2210/0076* (2013.01)

(58) Field of Classification Search
   CPC ............. A61F 2/16; A61F 2002/061; A61F 2002/065; A61F 2002/075; A61F 2/852;
   (Continued)

(56) References Cited

U.S. PATENT DOCUMENTS

2003/0199967 A1   10/2003   Hartley et al.
2006/0247761 A1   11/2006   Greenberg et al.
(Continued)

FOREIGN PATENT DOCUMENTS

CN   102488575 A   6/2012
CN   203841852 U   9/2014
(Continued)

OTHER PUBLICATIONS

International Search Report dated Nov. 29, 2018 in corresponding International application No. PCT/CN2018/101738; 4 pages.
(Continued)

*Primary Examiner* — Paul B Prebilic
(74) *Attorney, Agent, or Firm* — Maier & Maier, PLLC (57) ABSTRACT

A covered stent includes a tubular main stent and a connection stent disposed on the main stent. An opening is formed in a side wall of the main stent. The connection stent includes a fixed segment connected to the side wall of the main stent and a free segment connected to the fixed segment. Each of the fixed segment and the free segment further includes a stent and a coating covering the surface of the stent. One end of the free segment distant from the fixed segment is connected to the edge of the opening, and a gap is formed between one side of the free segment near to the side wall of the main stent and the side wall of the main stent. This stent can effectively resolve the problem of the limitation of an adjusted angle at a connection segment of an external connection stent and has better flexibility.

21 Claims, 8 Drawing Sheets

(58) Field of Classification Search
CPC .......... A61F 2002/826; A61F 2002/828; A61F 2/856; A61F 2/90; A61F 2210/0076; A61F 2220/0075; A61F 2250/0059; A61F 2250/006; A61F 2250/0062; A61F 2250/0063

See application file for complete search history.

(56) References Cited

U.S. PATENT DOCUMENTS

| | | | |
|---|---|---|---|
| 2008/0275548 A1 | 11/2008 | Svensson | |
| 2009/0048663 A1* | 2/2009 | Greenberg | A61F 2/07 623/1.35 |
| 2009/0222077 A1 | 9/2009 | Caldarise et al. | |
| 2009/0319022 A1 | 12/2009 | Hartley et al. | |
| 2013/0138199 A1* | 5/2013 | Ivancev | A61F 2/95 623/1.11 |
| 2013/0226282 A1 | 8/2013 | Ahn et al. | |
| 2013/0274857 A1* | 10/2013 | Quinn | A61F 2/07 623/1.11 |
| 2016/0081787 A1* | 3/2016 | Parodi | A61F 2/07 623/1.14 |
| 2016/0184115 A1 | 6/2016 | Ondersma et al. | |
| 2017/0056216 A1* | 3/2017 | Khoury | A61F 2/07 |

FOREIGN PATENT DOCUMENTS

| | | |
|---|---|---|
| CN | 105769383 A | 7/2016 |
| CN | 105943199 A | 9/2016 |
| EP | 3 150 167 A1 | 4/2017 |
| EP | 3 187 148 A1 | 7/2017 |
| EP | 3 421 009 A1 | 1/2019 |
| WO | 2016/183128 A1 | 11/2016 |

OTHER PUBLICATIONS

Extended European Search Report dated Aug. 19, 2021, in connection with corresponding EP Application No. 18852005.0; 13 pages.
Partial Supplementary European Search Report dated Apr. 28, 2021, in connection with corresponding EP Application No. 18852005.0; 15 pages.
Indian Office Action dated May 28, 2021, in connection with corresponding IN Application No. 202017011330; 5 pages.

* cited by examiner

COVERED STENT

FIELD

Embodiments relate to the field of cardiovascular medical instruments, in particular to a covered stent.

BACKGROUND

In the prior art, in order to solve the problem of involvement of bifurcated vessels in a lesion site, a covered stent fenestrated technology is generally used, which can isolate the lesion vessels but also keep the bifurcated vessels clear. However, the technology still has the problems of difficult bifurcated port positioning, poor connection matching between branches and a main body, poor angle adaptability after placement of connection stent and the like, and how to effectively connect the branches and the main body to achieve an ideal effect of isolation and shunt is a research direction of this technology.

In-situ fenestrated technology of a covered stent is a technology that first inserts a complete coating main body, then introduces a physical puncture or laser breakdown to punch holes at branch positions, and finally introduces a connection stent. The technology is feasible in theory, but there are some problems in practice, such as debris falling off in the holes punching process, uncontrollability of the hole size, and possible thrombosis and the like during the fenestrated process.

In view of the above problems, the Chinese patent with the publication number of CN203841852U proposes a fenestrated side branch covered stent, namely, a short branch of a transition segment is placed in a position to be opened in the main stent in advance, and a polymer flexible segment is used to connect the opening position at the adjacent opened position, so as to connect with the short branch. The method can be positioned through the short branch of transition segment, and can be well connected through the polymer flexible segment. Compared with a covered stent with only a short branch of rigid built-in transition segment, the covered stent can adjust the connection angle with the short branch within a certain range, such that the risk of endoleak caused by loose connection position can be effectively avoided. However, due to the fact that the polymer flexible segment lacks metal stent support and is placed in the covered stent, it may cause the risk of branch blood supply shortage due to branch closure under the impact of blood flow, which increases the burden of patients' self-healing. In addition, the polymer flexible segment in the patent is completely fixed to the main body stent, and when a branch stent is externally connected, an adjusted angle of the branch stent can be limited to a certain extent.

The Chinese patent application with the publication number of CN 102488575A provides an aorta fenestration stent, which opens a side window at a coating portion of a main stent without a metal framework and introduces a small stent with a metal framework support into the inner wall of the side window, and the axis of the small stent is parallel to the axis of the main stent, and the small stent serves to connect the main stent and a branch stent. The metal framework of the small stent 3 improves the radial support force of the small stent and can effectively fix branch channels, but reduces the flexibility of the small stent. When the branch stent is introduced and connected with the small stent, the branch stent is easily restrained at the joint of being connected with the small stent, especially for complex branch vessels having a large degree of bending. Moreover, the compatibility between the branch stent and the small stent is poor, which may lead to a risk of typeIendoleak. In addition, there is also the problem that the local stress in the connection section is too high and the branch vessels are pressed.

SUMMARY

Embodiments described herein provide a covered stent which can effectively fix the external branch stent and has good flexibility addressing the defects of the prior art.

A technical solution adopted to solve technical problems thereof is to configure a covered stent which includes a tubular main stent and a connection stent disposed on the main stent.

An opening is formed in a side wall of the main stent. The connection stent includes a fixed segment connected to the side wall of the main stent and a free segment connected to the fixed segment. Each of the fixed segment and the free segment includes a stent and a coating covering the surface of the sent. One end of the free segment distant from the fixed segment is connected to the edge of the opening, and a gap is formed between one side of the free segment near to the side wall of the main stent and the side wall of the main stent.

The covered stent of the application introduces the connection stent inside the main stent, and the fixed segment and the free segment of the connection stent are provided with the stent, so as to ensure the support force of the connection stent in the radial and axial directions, and avoid the risk of channel closure due to the impact pressure of blood flow. Further, the two ends of the free segment are connected to the fixed segment and the edge of the opening of the main stent, while the middle portion of the free segment is not fixed to the side wall of the main stent. Compared with a general fenestrated stent, the covered stent can effectively solve the problem of the limitation of an adjusted angle of an external connection stent at the connection segment. Therefore, the covered stent of the application can be suitable for various complicated and changeable branch vessel configurations, and has the advantages of good universality, simple structure and the like.

In addition, a corresponding number of the connection stents can be introduced according to the number of branch vessels at a specific lesion site, and if there is no lesion in the branch vessels, the connection stent serves only as a drainage to prevent series of complications caused by the closure of the branch vessels; if branches involve a lesion, an external branch stent can be introduced at the branch fracture, which can be used in conjunction with the connection stent to play an isolation effect and achieve the purpose of treatment.

BRIEF DESCRIPTION OF THE DRAWINGS

The present application will now be further described with reference to the accompanying drawings and embodiments, in which:

FIG. 6 is a top view of an extension segment of the covered stent shown in FIG. 5a;

DETAILED DESCRIPTION OF EMBODIMENTS

Figure 1:
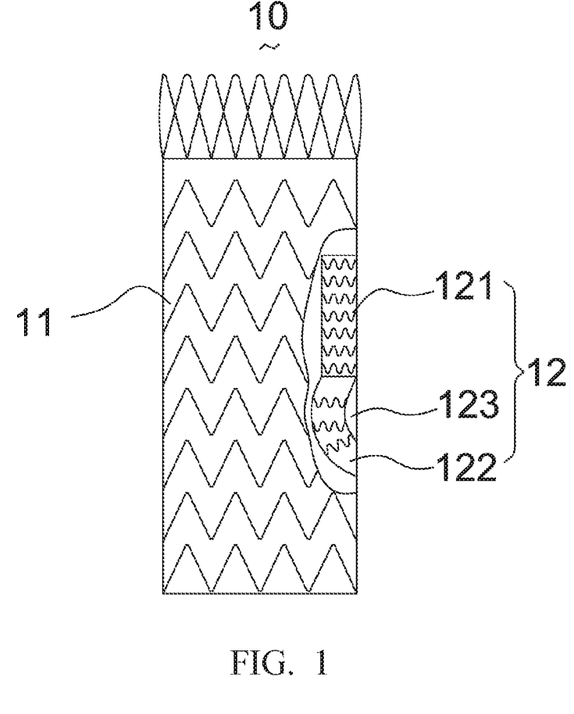
FIG. 1 is a front view of a preferred embodiment of a covered stent.
Figure 8:
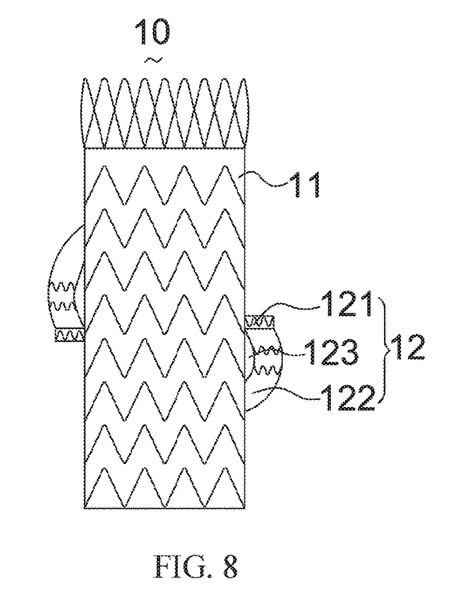
FIG. 8 is a front view of yet another embodiment of a covered stent.

The technical features, purposes and effects of the present disclosure will be more clearly understood from the following detailed description of the embodiments with reference to the accompanying drawings. As shown in FIGS. 1 and 8, a covered stent 10 includes a tubular main stent 11 and a connection stent 12 disposed on the main stent 11 and connected to the main stent 11. An opening O is formed in a side wall of the main stent 11. The connection stent 12 includes a fixed segment 121 connected to the side wall of the main stent 11 and a free segment 122 connected to the fixed segment 121. One end of the free segment 122 distant from the fixed segment 121 is connected to the edge of the opening O, and a gap 123 is formed between one side of the free segment 122 near to the side wall of the main stent 11 and the side wall of the main stent 11. The covered stent 10 has a radial expansion capability and may be compressed under the action of an external force and self-expand after the withdrawal of the external force or restore to the original shape and maintain the original shape by mechanical expansion, such as balloon expansion. Thus, after being implanted into a lumen, the covered stent 10 can be tightly attached to a wall of the lumen and may be fixed in the lumen through its radial support force, thereby playing the roles of reconstructing a blood flow channel and isolating the lesion.

Figure 2:
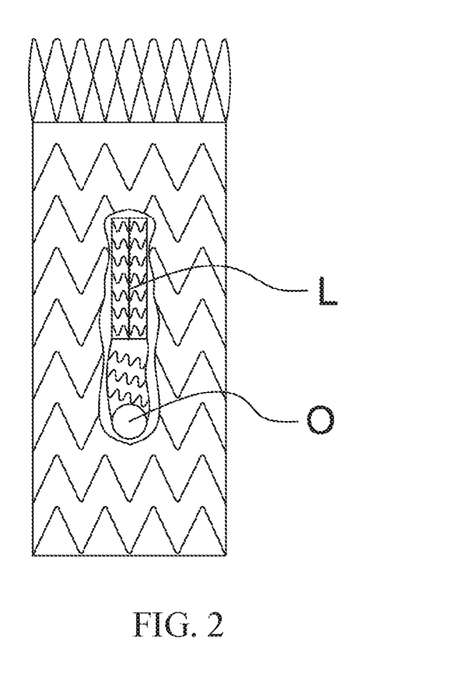
FIG. 2 is a right side view of the covered stent shown in FIG. 1.
Figure 3:
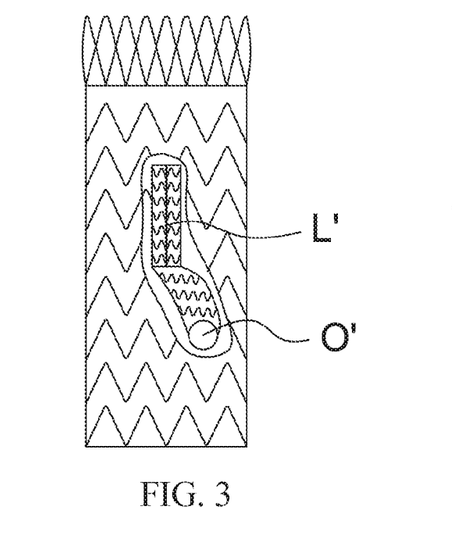
FIG. 3 is a front view of another embodiment of a covered stent.
Figure 4:
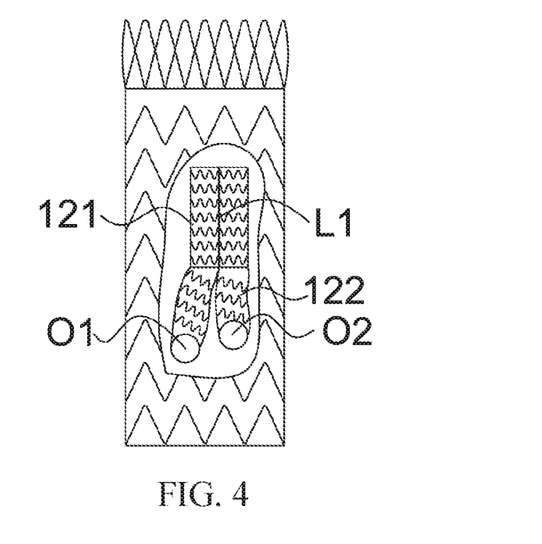
FIG. 4 is a front view of yet another embodiment of a covered stent.

As shown in FIGS. 1 and 2, the connection stent 12 is integrally positioned inside the lumen of the main stent 11, and the fixed segment 121 is fixed on an inner side wall of the main stent 11 and has a connection line L with the inner side wall of the main stent 11. The proximal end of the free segment 122 is connected to the fixed segment 121, and the distal end thereof is connected to the edge of the opening O through the inner and outer side walls of the main stent 11. And a gap 123 is formed between one side of the free segment 122 near to the inner side wall of the main stent 11 and the inner side wall of the main stent 11. In this embodiment, the center of the opening O falls on an extension line of the connection line L of the fixed segment 121 and the inner side wall of the main stent 11. As shown in FIG. 3, in another embodiment, the center of an opening O' may also deviate from a connection line L' of the fixed segment 121 and the inner side wall of the main stent 11. A part of the blood flowing into the lumen of the main stent 11 flows out of the opening O through the connection stent 12, and the blood flowing out of the opening O is supplied the branch vessels via an external stent. The position of the center of the opening O with respect to the connection line L may not only control the flow rate of blood flowing through the connection stent 12 so as to achieve a blood pressure fine-tuning effect and match the flow rate of normal branch vessels, but also avoid implantation difficulty caused by overlap of the two connection stents 12 when the branch vessels are close to each other. For example, it can be set according to the actual condition of a patient, and in the end, the blood flow within the connection stent 12 may be guaranteed and the blood flow rate within the connection stent 12 may be controlled. It can be noted that the opening O may be positioned between wave coils of the main stent 11 or on the wave coils of the main stent 11. For example, when the opening O is connected to two branch stents, the opening O may be positioned on the wave coils of the main stent 11, and the two branch stents are positioned on either side of the wave coil of the main stent 11, respectively. When the opening O are positioned between the wave coils of the main stent, due to the fact that there are morphological differences in blank areas of the coating between the wave coils, the binding force to the branch stent 5 is different when the opening O is connected to the branch stent 5 at different positions, and the branch stent 5 shows different bending angles macroscopically, indicating that the flexibility of the branch stent 5 may be fine-adjusted by changing the position of the opening O. In the embodiments shown in FIGS. 1 to 3, the number of the fixed segments 121 is equal to that of the free segments 122. It can be noted that in another embodiment, the number of the free segments 122 may be greater than the number of the fixed segments 121, and at least one of the fixed segment 121 is connected to a plurality of the free segments 122. This configuration may be used for branch openings with slow blood flow rate, more branches, and different orientations, and may be flexibly applied to main vessel lesions involving multiple branches. For example, as shown in FIG. 4, there is provided one fixed segment 121 and two free segments 122 with an opening O1 and an opening O2, and the fixed segment 121 and the inner side wall of the main stent 11 have a connection line L1, and the opening O1 and the opening O2 are positioned at either side of an extension line of the connection line L1, respectively.

Figure 5A:
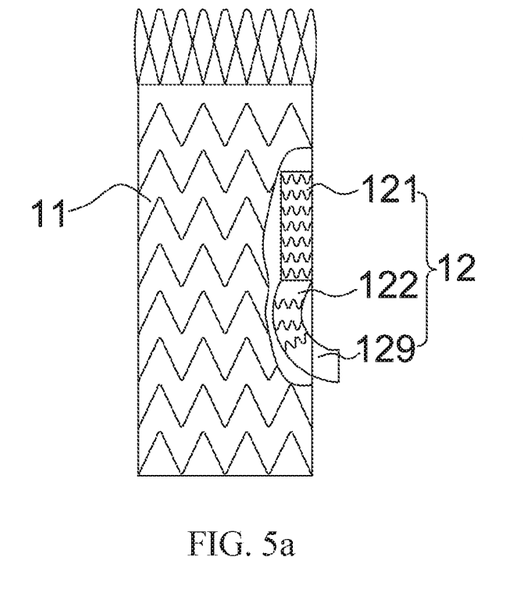
FIG. 5a is a front view of yet another embodiment of a covered stent
Figure 5B:
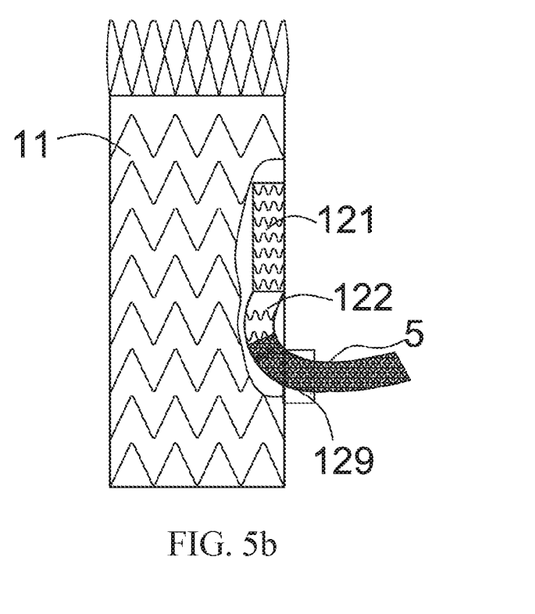
FIG. 5b is a schematic diagram of the structure of the covered stent of FIG. 5a in conjunction with a branch stent.
Figure 5C:
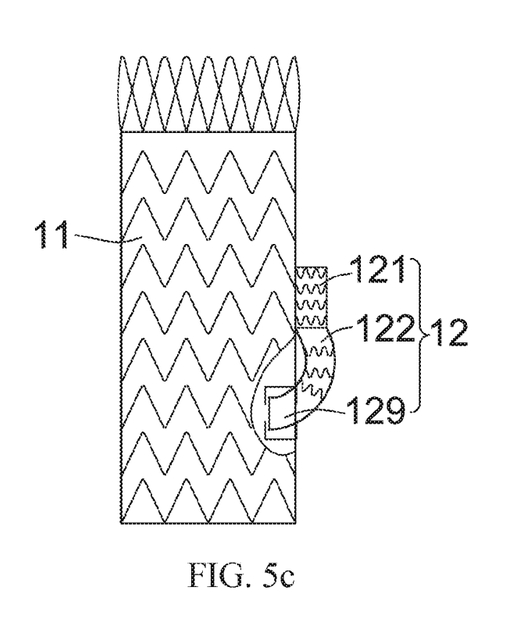
FIG. 5c is a front view of yet another embodiment of a covered stent
Figure 5D:
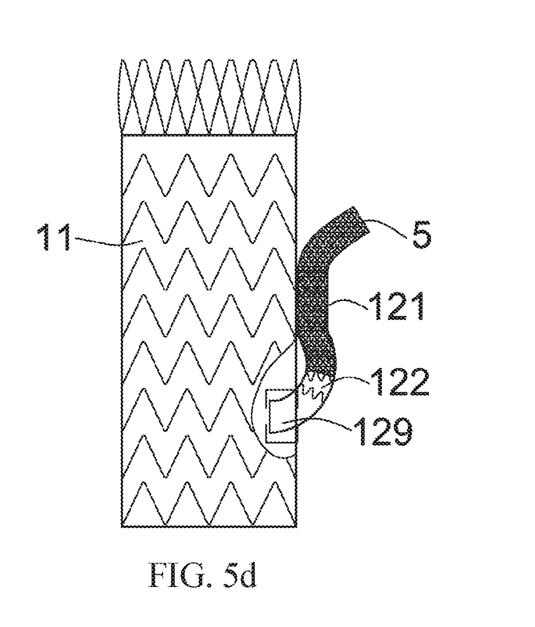
FIG. 5d is a schematic diagram of the covered stent of FIG. 5c in conjunction with a branch stent according to one embodiment.
Figure 5E:
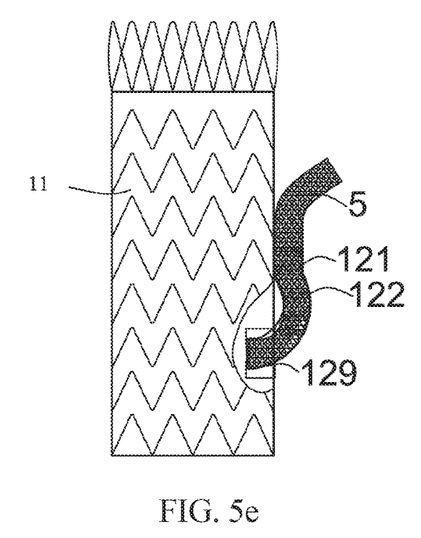
FIG. 5e is a schematic diagram of the structure of the covered stent of FIG. 5c in conjunction with the branch stent according to another embodiment.

As shown in FIGS. 5a and 5c, in one of the embodiments, the connection stent 12 further includes an extension segment 129 which connects to one end of the free segment 122 distant from the fixed segment 121 and extends out of the main stent 11 (as shown in FIG. 5a) or is positioned inside the main stent (as shown in FIG. 5c). In one of the embodiments, when the connection stent 12 is built-in as shown in FIG. 5a, the branch stent 5 may access the free segment 122 through the extension segment 129 and the opening of the main stent 11, with the actual effect as shown in FIG. 5b, at which point if the diameter of the connection stent 12 is smaller or the length of the free segment 122 is shorter, the length of the extension segment 129 may be appropriately extended to increase an anchor area of the branch stent 5 to improve the anchoring force thereof; if a tumor cavity at the lesion site is smaller, the length of the extension segment 129 may be appropriately reduced, and the specific condition may be set according to the actual conditions of the patient. In another embodiment, when the connection stent 12 is externally provided, as shown in FIG. 5c, the branch stent 5 may access the free segment 122 through the fixed segment 121 and the joint between the fixed segment 121 and the free segment 122, and the actual effect is as shown in FIG. 5d, at which point if the axial extension area of a tumor body is shorter, the length of the fixed segment 121 may be appropriately reduced, and the extension segment 129 only serves as a branch shunting, and the length of the extension segment 129 may be appropriately reduced, or the extension segment 129 may even be eliminated; if the volume of the tumor cavity is further reduced, the branch stent 5 may be directly passed through the connection stent 12, with an effect shown in FIG. 5e, at which point the effect is similar to that of a chimney stent, and the specific condition may be set according to actual conditions of the patient. It can be noted that an angle of the connection port of the branch stent 5 at the opening of the free segment or the extension segment may be adjusted in the above two cases. In addition, the lengths of the fixed segment 121, the free segment 122 and the extension segment 123 may be adjusted according to the design, which indicates that the design may be applied to various complex branch by-passes.

Figure 6:
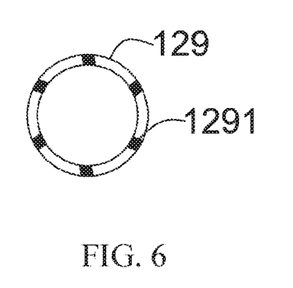
Figure 7A:
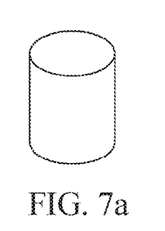
FIG. 7a is a schematic diagram of the structure of the extension segment of the covered stent shown in FIG. 5 of the present application.
Figure 7B:
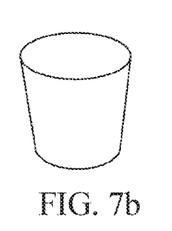
FIG. 7b is a schematic diagram of the structure of the extension segment of the covered stent shown in FIG. 5 of the present application.
Figure 7C:
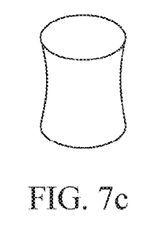
FIG. 7c is a schematic diagram of the structure of the extension segment of the covered stent shown in FIG. 5 of the present application.
Figure 7D:
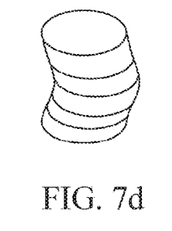
FIG. 7d is a schematic diagram of the structure of the extension segment of the covered stent shown in FIG. 5 of the present application.

With further reference to FIG. 6, one end of the extension segment 129 distant from the free segment 122 is provided with a developing mark 1291, by which the end position of the connecting stent 12 may be accurately determined to facilitate a doctor to access the branch stent 5 on the connecting stent 12. The number and shape of the developing mark 1291 may be adjusted and designed according to actual conditions. The extension segment may have a variety of shapes, as shown in FIGS. 7a to 7d, the extension segment 129 may be of a cylindrical shape with the same size at both ends (as shown in FIG. 7a), the extension segment 129 may also be of a truncated cone shape with different sizes at both ends (as shown in FIG. 7b), and the extension segment 129 may also be of an hourglass shape with the same size at both ends and gradually reducing from both ends to the middle position (as shown in FIG. 7c), and the extension segment 129 may also be of an angular shape in which the center lines of both ends are not in the same straight line (as shown in FIG. 7d). It can be appreciated that FIGS. 7a-7d are only illustrative of the shape of the extension segment 129 and are not limitations of the embodiments, and that those of ordinary skill in the art may adjust the shape of the extension segment 129 according to actual conditions.

It can also be appreciated that the surface of the extension segment 129 may be further provided with a self-expanding or ball-expanding metal framework, and the length of the extension segment 129 may be adjusted according to actual needs.

As shown in FIG. 8, in another embodiment, the connection stent 12 is integrally positioned outside a lumen of the main stent 11, the fixed segment 121 is fixed on an outer side wall of the main stent 11, one end of the free segment 122 is connected to the fixed segment 121 and the other end is connected to the edge of an opening O of the main stent 11, and a gap 123 is formed between one side of the free segment 122 near to the outer side wall of the main stent 11 and the outer side wall of the main stent 11. In addition, the opening direction of the connection stent 12 is adjustable.

Figure 9:
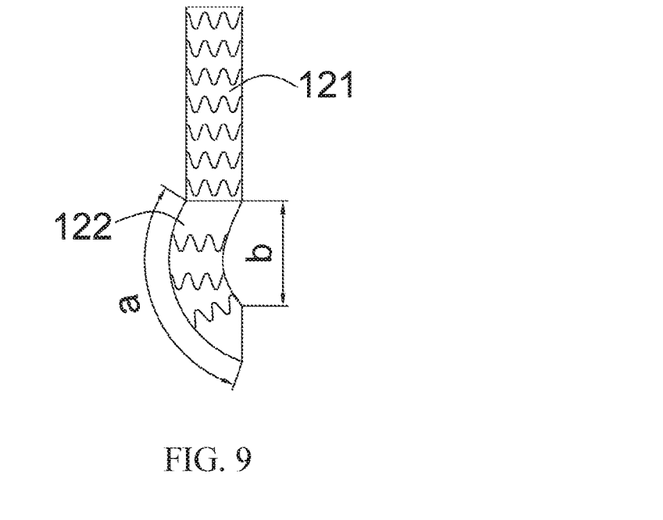
FIG. 9 is a schematic diagram of the structure of a connection stent in the covered stent shown in FIG. 1.

Each of the fixed segment 121 and the free segment 122 includes a stent and a coating covering the surface of the sent. The stent of the fixed segment 121 can effectively exert radial and axial support, and one side of the fixed segment 121 is integrally connected with a side wall of the main stent 11, thereby stabilizing a channel of the fixed segment 121, preventing the channel of the fixed segment 121 from closing under the impact pressure of blood flow. In the assembly state, the length a of the coating of one side of the free segment 122 distant from the side wall of the main stent 11 is greater than the shortest vertical distance b from the proximal end to the distal end of the coating (as shown in FIG. 9), and a gap is formed between wave coils of the stent of the free segment 122. This configuration not only enables the free segment 122 to be axially stretched, but also provides radial support for the coating of the free segment 122 to avoid the channel closure of the free segment 122. In addition, when an external branch stent is provided, the proximal end of the external branch stent is in the free segment 122, and due to the fact that a gap 123 is formed between one side of the free segment 122 near to the main stent 11 and the side wall of the main stent 11, when an angle of the external branch stent needs to be adjusted, the gap 123 between the free segment 122 and the main stent 11 may provide space for the angle adjustment of the external branch stent. In one of the embodiments, the diameter of the free segment 122 is greater than the diameter of the fixed segment 121. After the branch stent is introduced into the free segment 122, by increasing the diameter of the free segment 122, the blood flow cross-section of the branch stent may be increased under the condition that the blood flow of the main stent 11 remains unchanged. Further, when the diameter of the branch stent is large, it may be well matched with the branch stent without affecting the diameter of a sheath required by the main stent 11, so as to reduce the occurrence of endoleak.

In order to further improve the flexibility of the free segment 122, the embodiments further improve the stent structure of the free segment 122, as illustrated particularly by the following:

The First Embodiment

Figure 10:
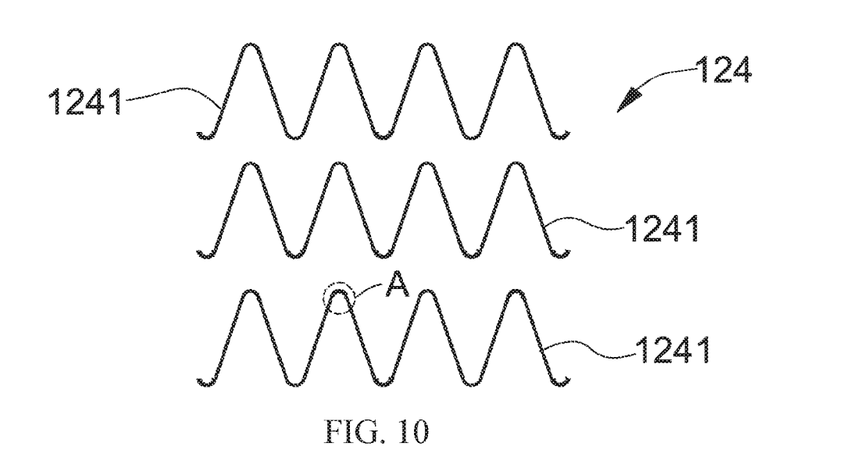
FIG. 10 is an expanded view of a first embodiment of a stent of a free segment of the covered stent shown in FIG. 1.
Figure 11:
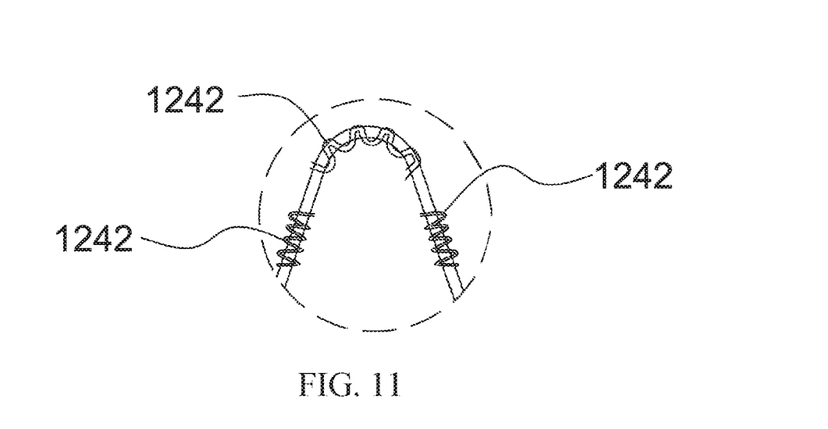
FIG. 11 is an enlarged view of a portion A of FIG. 10.

As shown in FIG. 10, a stent 124 of a free segment 122 includes a number of waveform rings 1241 spaced along its generatrix, and, in this embodiment, the waveform phases of the number of the waveform rings 1241 are the same. In other possible embodiments, the waveform phases of the number of the waveform rings may also be opposite. As shown in FIG. 11, the number of the waveform rings 1241 are connected to the coating of the free segment 122 only at positions of crests and/or troughs thereof by sutures or band-shaped coating 1242. Advantages of being connected to the coating only at the positions of the crests and/or troughs are that the channel closure of the free segment may be avoided and the flexibility of the free segment 122 is maintained to a maximum extent due to the fact that the number of connection points between the stent 124 and the coating is minimized, and when the free segment is axially compressed, the coating may be compressed to a maximum extent and its shape is changed more freely. Not all the crests and the troughs are connected to the coating, and several crests and/or troughs may be selectively connected to the coating. The number of the waveform rings 1241 are spaced apart and have the same waveform phase.

When subjected to an axial compressive force, the crest of one of the waveform rings 1241 may extend into the middle of the two troughs of the waveform rings adjacent thereto, thereby improving the flexibility of the free segment 122.

The Second Embodiment

Figure 12:
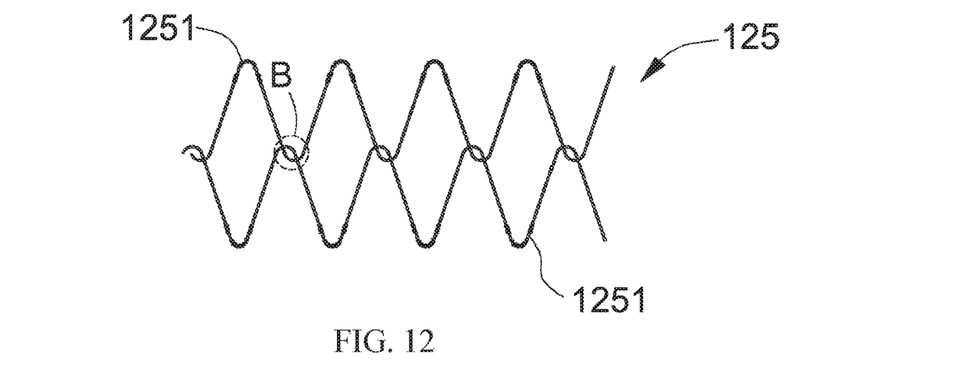
FIG. 12 is an expanded view of a second embodiment of the stent of the free segment of the covered stent shown in FIG. 1.
Figure 13:
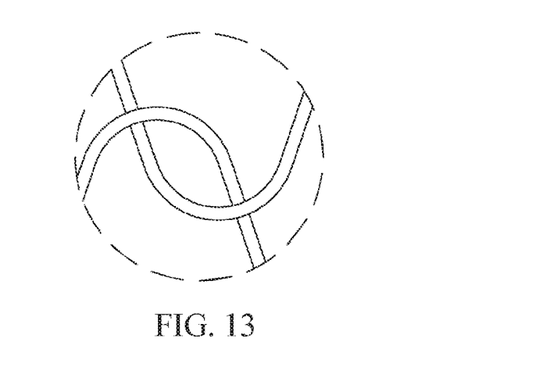
FIG. 13 is an enlarged view of a portion B of FIG. 12 of the present application.

As shown in FIG. 12, a stent 125 of a free segment 122 includes a number of waveform rings 1251, and the waveform phases of two adjacent waveform rings 1251 are opposite, and crests and troughs of the two adjacent waveform rings 1251 are interlocked. The interlocking arrangement refers to the structure as shown in FIG. 13. The wire forming the crest portion of a second waveform ring 1251 in FIG. 7 passes over the wire forming the trough portion of a first waveform ring 1251 in FIG. 12, and then comes out from under the wire forming the trough portion. The number of fixing points may be reduced by connecting the two adjacent waveform rings through the interlocking structure rather than through sutures, and the interlocking structure allows for axial expansion and fine-tuning between the two adjacent waveform rings 1251 so as to be conveniently mated with various complicated external branch stents and improve the flexibility of the free segment 122. In addition, by setting the number and the spacing of the waveform rings, and adjusting the wire diameter, the wave number and the height of the waveform rings, the radial support may be controlled, and the axial local fine-tuning may be achieved.

Figure 14:
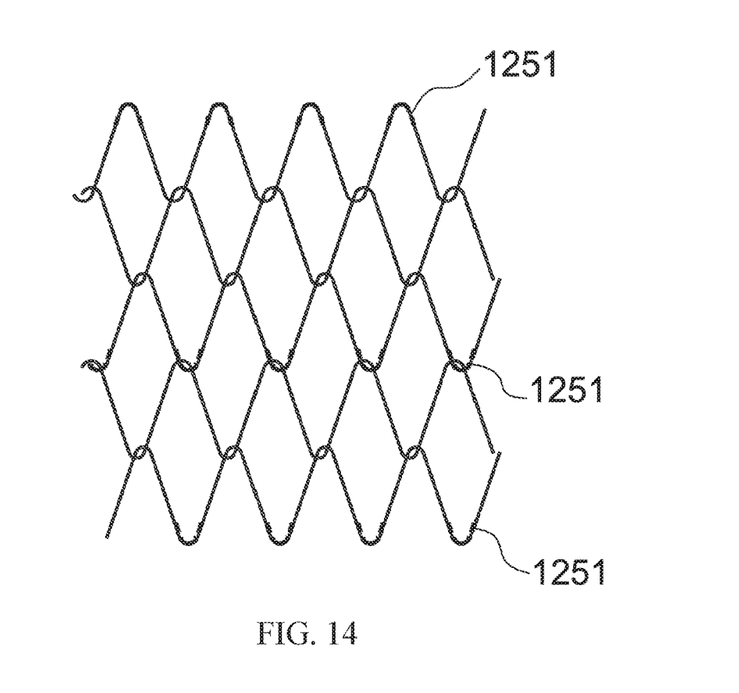
FIG. 14 is an expanded view of a third embodiment of the stent of the free segment of the covered stent shown in FIG. 1.

In addition, when the waveform rings 1251 of the stent 125 is relatively small in number, the crests or troughs of the two waveform rings 1251 fore and aft may be fixed only by the sutures or the band-shaped coating; as shown in FIG. 14, when the free segment 122 is longer, with the increasing of the waveform rings 1251 of the stent 125, there might be a risk that the waveform rings in the middle part may be tilted away from the coating if only the crests or troughs of the two waveform rings 1251 fore and aft are fixed, therefore, it may be desirable to select one or more of the waveform rings between the two waveform rings 1251 fore and aft and fix the crests or troughs thereof to the coating by sutures.

The Third Embodiment

Figure 15:
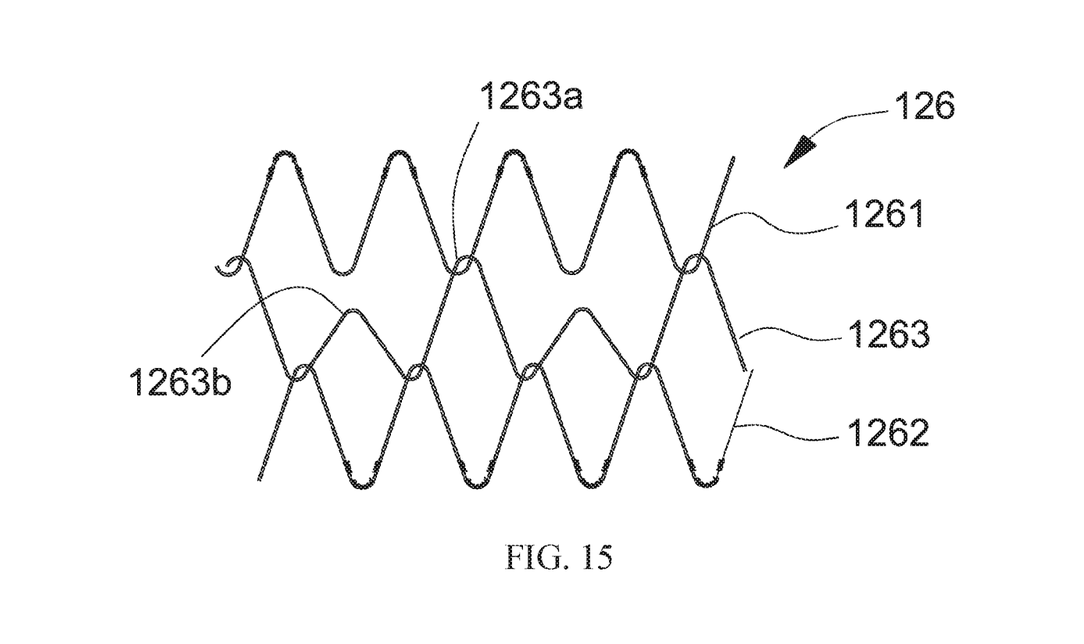
FIG. 15 is an expanded view of a fourth embodiment of the stent of the free segment of the covered stent shown in FIG. 1.
Figure 16:
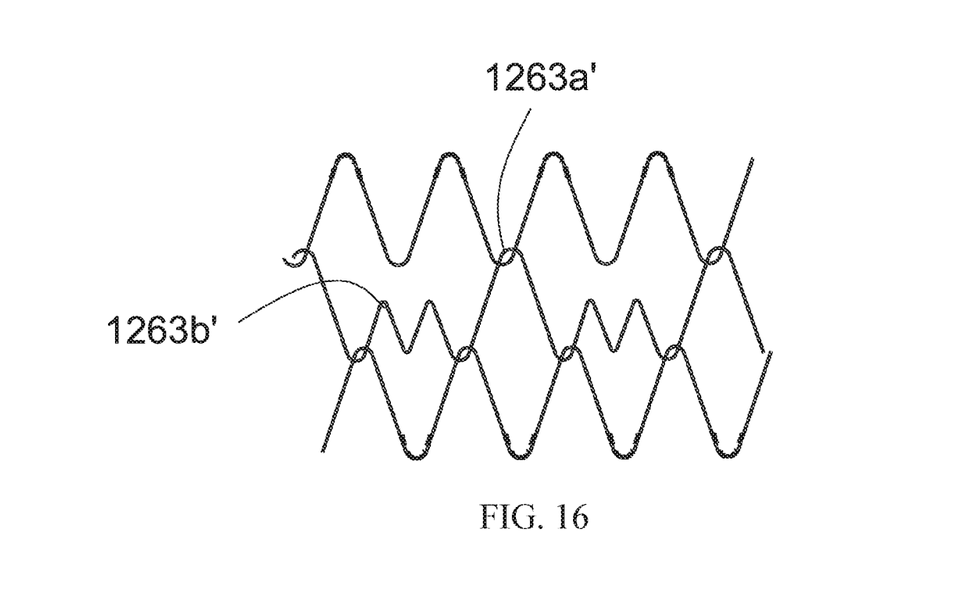
FIG. 16 is an expanded view of a fifth embodiment of the stent of the free segment of the covered stent shown in FIG. 1.

As shown in FIG. 15, on the basis that any two adjacent waveform rings in the previous embodiment are interlocked, a stent 126 of a free segment in this embodiment includes a first waveform ring 1261, a second waveform ring 1262, and a third waveform ring 1263 positioned between the first waveform ring 1261 and the second waveform ring 1262. The third waveform ring 1263 has an unequal height waveform. The third waveform ring 1263 includes a number of first crests 1263a near to the first waveform ring 1261 and a number of second crests 1263b distant from the first waveform ring 1261, and the first crests 1263a and the second crests 1263b are spaced circumferentially along the third waveform ring 1263. And the apices of all the first crests 1263a fall on a plane perpendicular to the axis of the third waveform ring 1263, and the apices of all the second crests 1263b fall on another plane perpendicular to the axis of the third waveform ring 1263. All apices of the troughs of the third waveform ring 1263 fall on the same plane perpendicular to its axis. In this embodiment, a second crest 1263b is provided between any two adjacent first crests 1263a, as shown in FIG. 16, two second crests 1263b' may further be provided between any two adjacent first crests 1263a'. That is, the wave height of the third waveform ring 1263 varies periodically. Further, the first crest 1263a interlocks with the trough of the first waveform ring 1261, and the trough of the third waveform ring 1263 interlocks with the crest of the second waveform ring 1262. The third waveform ring 1263 has more wave numbers than the first waveform ring 1261 and the second waveform ring 1262 adjacent thereto, and while using the interlock structure to improve the flexibility, more wave numbers increase the contact area between the stent and the coating, so that the adhesiveness is better.

The Fourth Embodiment

Figure 17:
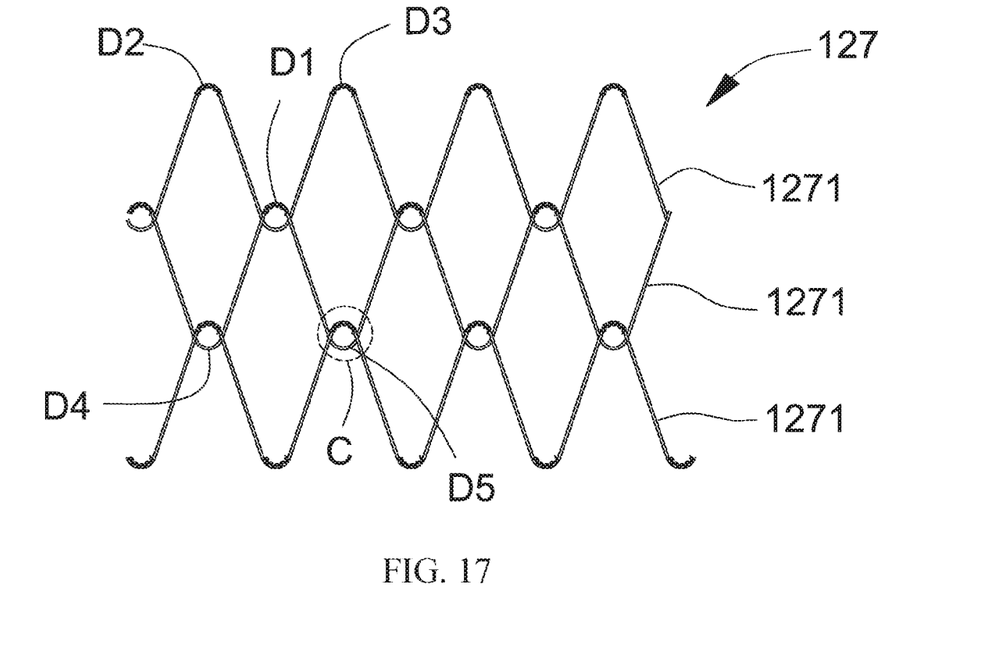
FIG. 17 is an expanded view of a sixth embodiment of the stent of the free segment of the covered stent shown in FIG. 1.
Figure 18:
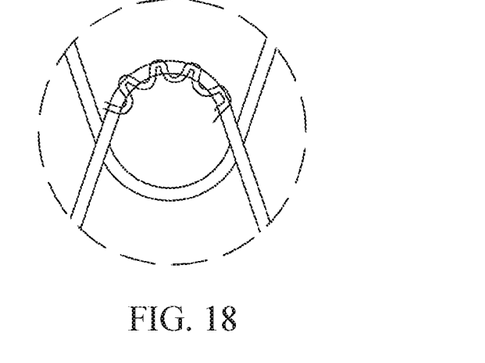
FIG. 18 is an enlarged view of a portion C of FIG. 17.

As shown in FIGS. 17 and 18, a stent 127 of a free segment in this embodiment includes a number of waveform rings 1271, the waveform phases of any two adjacent waveform rings being opposite. Different from the previous embodiment, the crest or trough of one of any two adjacent waveform rings 1271 is disposed on the trough or crest of the other waveform ring and is connected to the coating. FIG. 12 shows that the crest of the second waveform ring 1271 is disposed on the trough of the first waveform ring 1271 and is connected to the coating by the sutures.

As shown in FIG. 17, in a circular area centered on a fixed point D1, four additional fixed points D2, D3, D4 and D5 are distributed. When the waveform where the fixed points D1, D2 and D3 are located is compressed in the free segment, the motion of the waveform is limited only by the above five fixed points, the waveform may move within the wave height range of the waveform where the fixed points D1, D4 and D5 are located. Therefore, the flexibility is better than that of the above-described embodiments.

Figure 19:
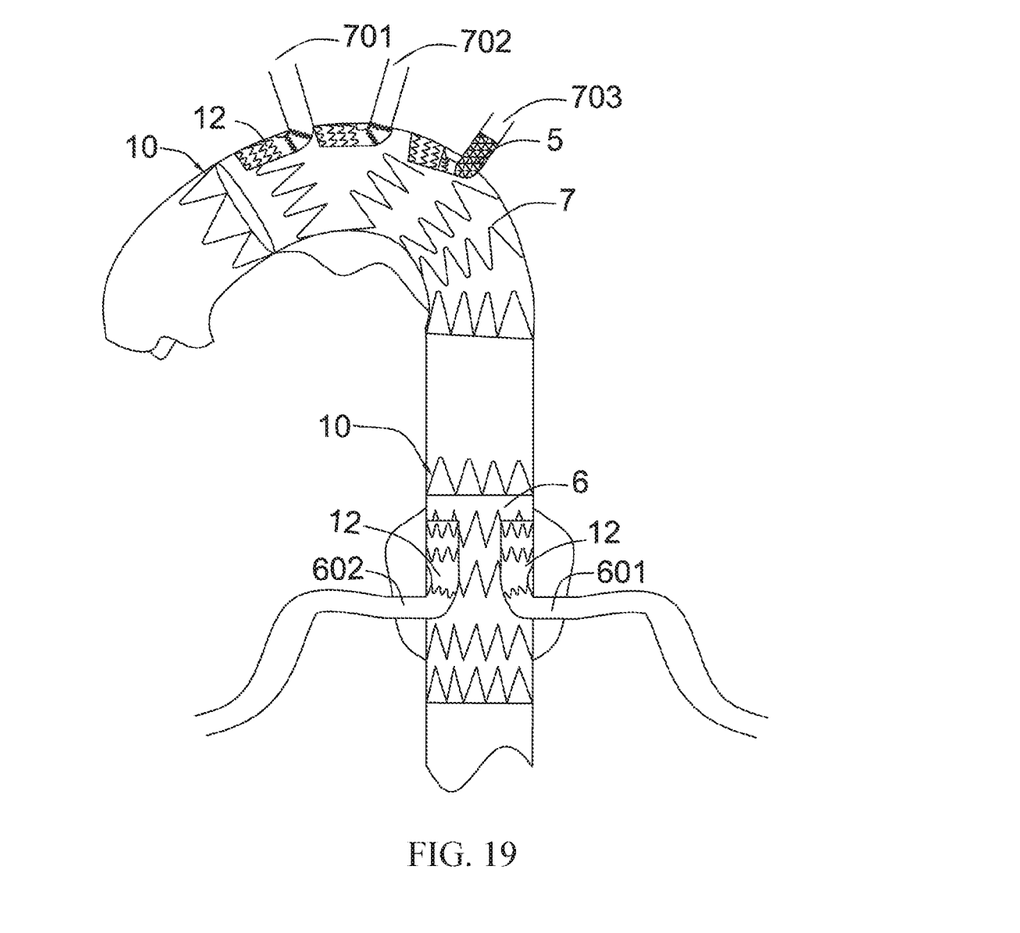
FIG. 19 is a schematic diagram of the effect of the covered stent being implanted into an aortic arch and its branch vessels.

FIG. 19 is a schematic diagram showing the effect of the covered stent 10 applied to the aortic arch 7 and its branches 701, 702 and 703, and the renal artery 6 and its branches 601 and 602 according to one embodiment of the present application. If there is no lesion in the branch vessels (e.g., 701 and 702), the connection stent 12 serves only as a drainage to prevent series of complications caused by the closure of the branch vessels; if the branches involve in a lesion (e.g., 703, 601, and 602), an external branch stent may be introduced at the branch fracture (an external stent 5 is introduced in a branch 703 as shown in FIG. 19) and used in conjunction with the connection stent 12 to play an isolation effect and achieve the purpose of treatment.

The covered stent in the embodiments introduces a connection stent on the main stent, a stent is provided at the fixed segment and the free segment of the connection stent, so as to ensure the radial and axial support force of the connection stent and avoid the risk of channel closure due to the impact pressure of blood flow. Moreover, the two ends of the free segment are connected with the fixed segment and the edge of the opening of the main stent while the middle portion of the free segment is not fixed on the inner side wall of the main stent, and compared with a general built-in fenestrated stent, the covered stent can effectively solve the problem of the limitation of an adjusted angle of an external connection stent at the connection segment. Therefore, the covered stent of the embodiments may be suitable for various complicated and changeable branch vessel configurations, and has advantages of good universality, simple structure, and the like.

Some embodiments of the application have been illustrated by the above-described embodiments, but should not be construed to limit the scope of the application. It can be noted that several variations and modifications may be made by those of ordinary skill in the art without departing from the spirit of the application, which fall within the scope of the application.

The invention claimed is:

1. A covered stent comprising:
a tubular main stent and a connection stent disposed on the main stent,
an opening being formed in a side wall of the main stent, wherein the connection stent comprises a fixed segment connected to the side wall of the main stent and a free segment connected to the fixed segment, each of the fixed segment and the free segment further comprising a stent and a coating covering the surface of the stent of each of the fixed segment and free segment,
one end of the free segment distant from the fixed segment being connected to the edge of the opening,
another end of the free segment being connected to the fixed segment,
and a gap being formed between one side of the free segment near to the side wall of the main stent and the side wall of the main stent,
wherein the fixed segment is fixed to the side wall of the main stent through a connection line connecting both ends of the fixed segment along an axial direction of the fixed segment,
a middle portion between the two ends of the free segment being not fixed to the side wall of the main stent; and
in an assembly state, the length of the coating of one side of the free segment distant from the side wall of the main stent is greater than a shortest vertical distance from a proximal end to a distal end of the coating.

2. The covered stent according to claim 1, wherein the fixed segment is fixed on an inner side wall of the main stent, the gap being formed between one side of the free segment near to the inner side wall of the main stent and the inner side wall of the main stent.

3. The covered stent according to claim 2, the connection stent further comprising an extension segment which connects to one end of the free segment distant from the fixed segment, and extends out of the main stent.

4. The covered stent according to claim 3, wherein one end of the extension segment distant from the free segment is provided with a developing mark.

5. The covered stent according to claim 1, wherein the fixed segment is fixed on an outer side wall of the main stent, and the gap being formed between one side of the free segment near to the outer side wall of the main stent and the outer side wall of the main stent.

6. The covered stent according to claim 1, wherein the stent of the free segment comprises a plurality of waveform rings spaced along a generatrix of the free segment, and the plurality of the waveform rings being connected to the coating of the free segment only at positions of crests and/or troughs thereof.

7. The covered stent according to claim 6, wherein two of the adjacent waveform rings are of the same or opposite phases.

8. The covered stent according to claim 1, wherein the stent of the free segment comprises a plurality of waveform rings, any two of the adjacent waveform rings being opposite in phase, and the crests and troughs of any two of the adjacent waveform rings are interlocked.

9. The covered stent according to claim 8, wherein, in the plurality of the waveform rings, the crests or the troughs of at least two of the waveform rings fore and aft are connected to the coating of the free segment.

10. The covered stent according to claim 9, the plurality of the waveform rings comprise a first waveform ring, a second waveform ring spaced apart from the first waveform ring, and a third waveform ring provided between the first waveform ring and the second waveform ring and connected to the first waveform ring and the second waveform ring; and
the third waveform ring having an unequal height waveform.

11. The covered stent according to claim 10, an apex of the crest of the third waveform ring comprising a first crest near to the first waveform ring and a second crest distant from the first waveform ring, and the first crest and the second crest being spaced circumferentially along the third waveform ring and falling on two planes perpendicular to an axis of the third waveform ring, respectively, and the apex of the trough of the third waveform ring falling on the same plane perpendicular to the axis of the third waveform ring; and
the first crest near to the first waveform ring being interlocked with the trough of the first waveform ring, and the trough of the third waveform ring being interlocked with the crest of the second waveform ring.

12. The covered stent according to claim 11, wherein two second crests are provided between any two of the adjacent first crests.

13. The covered stent according to claim 1, the stent of the free segment comprising a plurality of waveform rings, any two adjacent waveform rings being opposite in phase, and the crest or trough of one of the waveform rings are disposed on the trough or crest of the other waveform ring, and the crest or trough disposed on the other waveform ring being connected with the coating of the free segment.

14. The covered stent according to claim 13, the plurality of the waveform rings comprising a first waveform ring, a second waveform ring spaced apart from the first waveform ring, and a third waveform ring between the first waveform ring and the second waveform ring and connected to the first waveform ring and the second waveform ring; the third waveform ring having an unequal height waveform.

15. The covered stent according to claim 14, an apex of the crest of the third waveform ring comprises a first crest near to the first waveform ring and a second crest distant from the first waveform ring, the first crest and the second crest being spaced circumferentially along the third waveform ring and falling on two planes perpendicular to an axis of the third waveform ring, respectively, and the apex of the crest of the third waveform ring falling on the same plane perpendicular to the axis of the third waveform ring; and
the first crest near to the first waveform ring being disposed on the trough of the first waveform ring and being connected with the coating, and the trough of the third waveform ring being disposed on the crest of the second waveform ring and being connected with the coating.

16. The covered stent according to claim 15, wherein two second crests are provided between any two of the adjacent first crests.

17. The covered stent according to claim 1, wherein a center of the opening deviates from an extension line of the connection line of the fixed segment and the main stent.

18. The covered stent according to claim 1, wherein the number of the free segments is more than the number of the fixed segments, and at least one of the fixed segments being connected to a plurality of the free segments.

19. The covered stent according to claim 1, wherein the main stent further comprising waveform rings, and the opening is positioned between waveform rings of the main stent.

20. The covered stent according to claim 1, wherein the main stent further comprising waveform rings, and the opening is positioned on the waveform rings of the main stent.

21. The covered stent according to claim 1, wherein a center of the opening falls on an extension line of the connection line of the fixed segment and the main stent.

* * * * *